US00PP29097P2

(12) United States Plant Patent
Eveleens

(10) Patent No.: US PP29,097 P2
(45) Date of Patent: Mar. 13, 2018

(54) ***HYDRANGEA* PLANT NAMED 'HORT 10-087-07'**

(50) Latin Name: *Hydrangea macrophylla*
Varietal Denomination: Hort 10-087-07

(71) Applicants: Horteve Breeding BV, De Kwakel (NL); Kolster Holding BV, Boskoop (NL)

(72) Inventor: Cornelis Pieter Eveleens, De Kwakel (NL)

(73) Assignees: HORTEVE BREEDING B.V., Aalsmeer (NL), part interest; KOLSTER HOLDING B.V., Boskoop (NL), part interest ( * ) Notice: Subject to any disclaimer, the term of this patent is extended or adjusted under 35 U.S.C. 154(b) by 0 days.

(21) Appl. No.: 15/330,659

(22) Filed: Oct. 24, 2016

(51) Int. Cl.
*A01H 5/00* (2006.01)

(52) U.S. Cl.
USPC ..... Plt./250

(58) Field of Classification Search
USPC ..... Plt./226, 250
See application file for complete search history.

(56) References Cited

PUBLICATIONS

UPOV-PLUTO: Plant Variety Database; Oct. 27, 2017, citations for 'hotr 10-087-07'. 1 page.*

* cited by examiner

*Primary Examiner* — Susan McCormick Ewoldt
*Assistant Examiner* — Karen M Redden
(74) *Attorney, Agent, or Firm* — Penny J. Aguirre

(57) ABSTRACT

A new cultivar of *Hydrangea macrophylla* plant named, 'Hort 10-087-07', that is characterized by its compact plant habit, its double flowers with a large number of sepals that are pink in color, and its star-shaped sterile flowers comprised of elongated shaped sepals (ovate-elliptic) with pointed tips.

2 Drawing Sheets

Botanical classification: *Hydrangea macrophylla.*
Varietal denomination: 'Hort 10-087-07'.

CROSS REFERENCE TO RELATED APPLICATIONS

This application is related to a plant breeders' rights application filed in Europe on Oct. 28, 2014, application No. 2014/2685 with the application later withdrawn. There have been no offers for sale anywhere in the world more than one year prior to the filing of this application, any sales less than one year were under the direction of the Inventor and no accessibility to one of ordinary skill in the art could have been derived from the printed plant breeder's rights documents.

This application is co-pending with a U.S. Plant Patent Application filed for a plant derived from the same breeding program that is entitled *Hydrangea* Plant Named 'Hort 10-87-01' (U.S. Plant patent application Ser. No. 15/330,657) and *Hydrangea* Plant Named 'Hort 10-080-01' (U.S. Plant patent application Ser. No. 15/330/660).

BACKGROUND OF THE INVENTION

The present invention relates to a new and distinct cultivar of *Hydrangea macrophylla* and will be referred to hereafter by its cultivar name, 'Hort 10-087-07'. 'Hort 10-087-07' represents a new bigleaf *hydrangea*, a perennial shrub grown for landscape use.

'Hort 10-087-07' was derived from an ongoing controlled breeding program directed by the Inventor. The objectives of the breeding program include developing new cultivars of *Hydrangea* with double flowers combined with compact plant habits and floriferous blooming habits. 'Hort 10-087-07' arose from a controlled cross made by the Inventor in Boskoop, The Netherlands in June of 2009 between unnamed proprietary plants in the Inventor's breeding program, reference no. 08-022-08 (not patented), as the female parent and reference no. 08-022-06 (not patented), as the male parent. 'Hort 10-087-07' was selected as a single unique plant from amongst the resulting seedlings in June of 2014.

Asexual propagation of the new cultivar was first accomplished by stem cuttings by the Inventor in Boskoop, The Netherlands in July of 2011. Asexual propagation by stem cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Hort 10-087-07' as a unique cultivar of *Hydrangea macrophylla.*

1. 'Hort 10-087-07' exhibits a compact plant habit.
2. 'Hort 10-087-07' exhibits double flowers with a large number of sepals that are pink in color.
3. 'Hort 10-087-07' exhibits star-shaped sterile flowers comprised of elongated shaped sepals (ovate-elliptic) with pointed tips.

Both the female and male parent of 'Hort 10-087-07' differ from 'Hort 10-087-07' in being lacecap type *hydrangeas* and in having single flowers. 'Hort 10-087-07' can be most closely compared to the *Hydrangea macrophylla* cultivars 'Hort 10-087-01' (copending U.S. Plant patent application Ser. No. 15/330,657) and 'Hort 10-080-01' (copending U.S. Plant patent application Ser. No. 15/330,660). Both cultivars are similar to 'Hort 10-087-07' in having star-shaped, double flowers. 'Hort 10-087-01' differs from 'Hort 10-087-07' in having sterile flowers that are slightly darker pink in color with sepals that are shorter and broader, and in having a more compact overall plant habit. 'Hort 10-080-01' differs from 'Hort 10-087-07' in having sepals that are pink with white margins.

BRIEF DESCRIPTION OF THE DRAWINGS

The accompanying colored photographs illustrate the overall appearance and distinct characteristics of the new *Hydrangea*. The photographs were taken of a plant two years in age as grown in a 4-liter container outside under a shade screen in Boskoop, The Netherlands.

The photograph in FIG. 1 provides a side view of the plant habit of 'Hort 10-087-07' in bloom.

Figure 1:
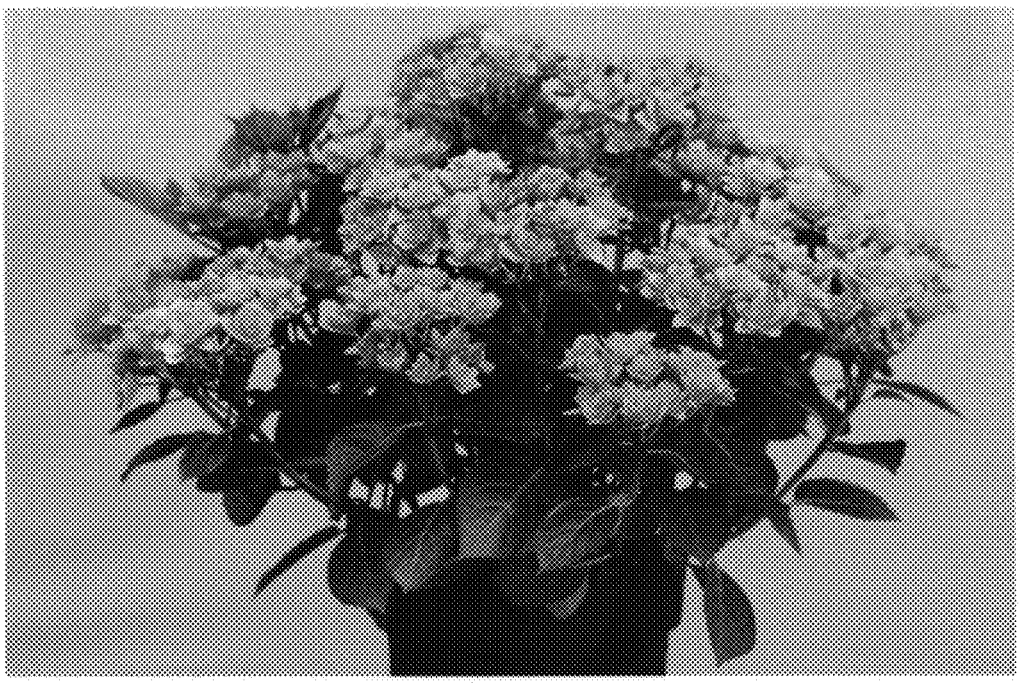
Figure 2:
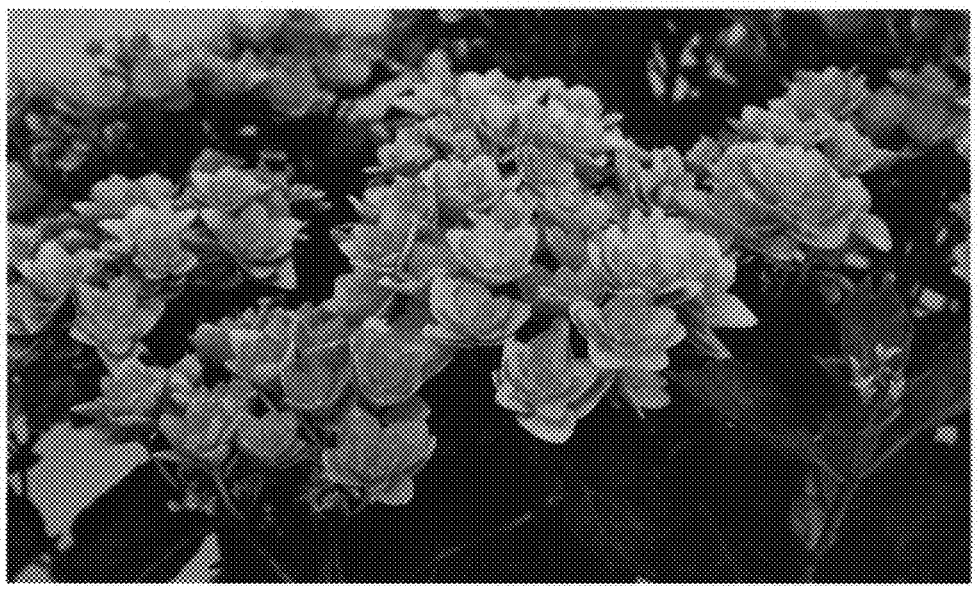

The photograph in FIG. 2 provides a close-up view of an inflorescence of 'Hort 10-087-07'.

Figure 3:
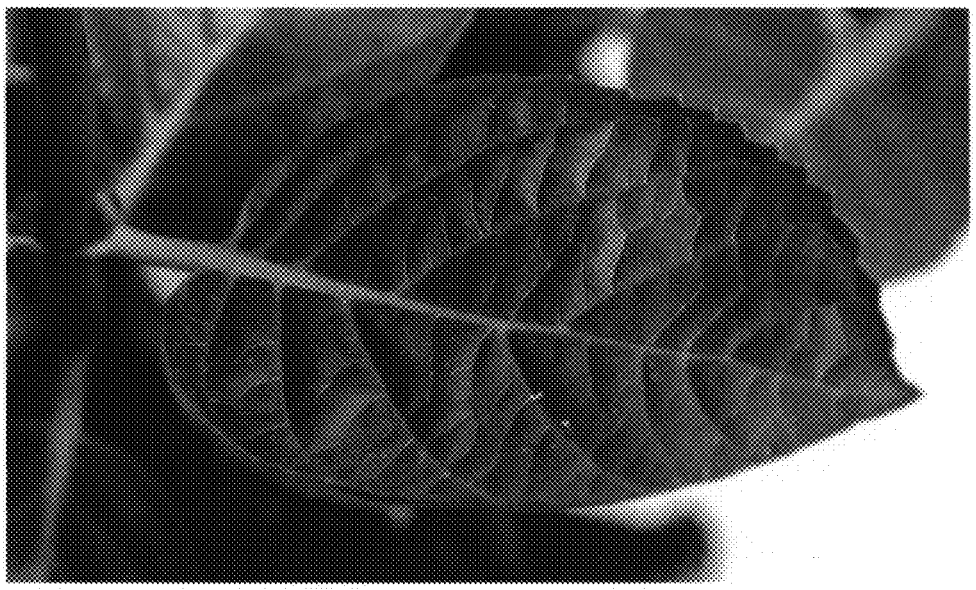

The photograph in FIG. 3 provides a close-up view of a leaf of 'Hort 10-087-07'.

The colors in the photographs are as close as possible with the photographic and printing technology utilized and the color values cited in the detailed botanical description accurately describe the colors of the new *Hydrangea*.

BOTANICAL DESCRIPTION OF THE PLANT

The following is a detailed description of plants two years in age as grown in 4-liter containers outside under a shade screen in Boskoop, The Netherlands. The phenotype of the new cultivar may vary with variations in environmental, climatic, and cultural conditions, as it has not been tested under all possible environmental conditions. The color determination is in accordance with The 2015 R.H.S. Colour Chart of The Royal Horticultural Society, London, England, except where general color terms of ordinary dictionary significance are used.

General description:

*Blooming period*.—From May to July in a greenhouse and from July to September outside in The Netherlands.

*Plant type*.—Perennial shrub, mophead-type *hydrangea*.

*Plant habit*.—Broadly spreading to upright, flattened globular shape.

*Height and spread*.—Up to 1 m in height and 1.5 m in spread.

*Hardiness*.—At least in U.S.D.A. Zones 5 to 9.

*Diseases and pests*.—No susceptibility and resistance to pests and diseases has been observed.

*Root description*.—Fibrous and fine, 199D in color.

*Propagation*.—Stem cuttings.

*Time required for root development*.—An average of 3.5 weeks for root initiation with a young rooted plant produced in an average of six months.

*Growth rate*.—Moderate.

Stem description:

*Stem shape*.—Rounded.

*Stem strength*.—Strong.

*Stem aspect*.—Upright to an average angle of 45° to soil.

*Stem color*.—Immature and mature stems; 144A suffused with a blend between N186A and 200A at the internodes, older bark; 199B to 199C.

*Stem size*.—An average of 18.3 cm (excluding the inflorescence) in length and 5 mm in diameter.

*Stem surface*.—Immature and mature stems; glabrous, glossy, and moderately lenticellate with lenticels; elliptic in shape, an average of 1 mm in length and 0.75 mm in width, and N186A in color.

*Branching*.—Well-branched with an average of 30 lateral branches, branching improves with pinching.

*Internode length*.—An average of 4.6 cm.

Foliage description:

*Leaf shape*.—Ovate to broadly ovate.

*Leaf arrangement*.—Opposite.

*Leaf division*.—Simple.

*Leaf number*.—An average of 6 (3 pairs) per lateral branch.

*Leaf base*.—Rounded to broadly cuneate.

*Leaf apex*.—Apiculate.

*Leaf margins*.—Lower ⅓ of leaf blade; entire, upper ⅔ of leaf blade; serrate.

*Leaf venation*.—Pinnate, color; upper surface 144C and lower surface; 145A.

*Leaf size*.—An average of 7.9 cm in length and 5.4 cm in width.

*Leaf attachment*.—Petiolate.

*Leaf surface*.—Upper surface; glabrous, moderately glossy, and moderately rugose, lower surface; glabrous, very slightly glossy, and moderately rugose.

*Leaf color*.—Young leaves; upper surface 144A and lower surface; 143C, mature leaves; upper surface; NN137A and lower surface 138A.

*Petioles*.—Flattened, an average of 1.3 cm in length and 3 mm in width, color; upper surface 144B to 144C and lower surface 144B with 144A towards the leaf node, both surfaces; glabrous, smooth and slightly to moderately glossy.

Inflorescence description:

*Inflorescence type*.—Flattened globular, mophead, compound corymb of rotate-shaped double sterile flowers.

*Lastingness of inflorescence*.—Sterile flowers; an average of 6 weeks, sepals persistent, fertile flowers; an average of 3 weeks, persistent.

*Inflorescence number*.—One per lateral stem.

*Inflorescence size*.—An average of 9.9 cm in height and 13.8 cm in diameter.

*Flower number*.—An average of 32 sterile flowers and 120 fertile flowers per inflorescence.

*Flower fragrance*.—None.

*Flower aspect*.—Sterile flowers; upright to outwards and drooping, fertile flowers; upright.

*Flower size*.—Sterile flowers; an average of 5 cm in diameter and 2.5 cm in depth, fertile flowers; an average of 7.5 mm in diameter and 7 mm in depth.

*Flower shape*.—Sterile and fertile flowers; irregular due to deformed gynoecia, overall obovate.

*Flower buds*.—Sterile flowers; an average of 1.2 cm in length and 7 mm in diameter, ovate in shape, color; 54C with base 150D, fertile flowers; an average of 4 mm in length and 2.5 mm diameter, obovate in shape, 144C lightly suffused with 174B to 174C towards the apex.

*Peduncles*.—An average of 4 cm in length and 3.5 mm in diameter, held upright, 144B in color, glabrous and smooth surface, strong.

*Pedicels*.—Sterile flowers; an average of 3.2 cm in length and 1.5 mm in diameter, held at an average angle of 27.5° to peduncle, 73B in color, strong strength, very slightly glossy surface is sparsely covered with short adpressed hairs; an average of 0.5 mm in length and NN155A in color, fertile flowers; an average of 5 mm in length and 0.75 mm in diameter, held at an average angle of 25° to peduncle, 148A to 148B in color, moderate strength, slightly glossy, smooth, and glabrous surface.

*Petals*.—Sterile flowers; not present, fertile flowers; an average of 4, rotate, ovate in shape, acute apex, cuneate base, entire margin, an average of 3 mm in length and 1.5 mm in width, color when opening and when fully open; upper surface 67C and lower surface 68B slightly suffused with 75B to 75C, color does not fade, both surfaces smooth and glabrous.

*Sepals*.—Sterile flowers; an average of 20, arrangement; rotate and double in four whorls, ovate to elliptic in shape, cuneate base, rounded to bluntly acute apex, entire margin, an average of 2 cm in length and 1.4 cm in width, color; upper surface when opening 58B to 58C, lower surface when opening 63B, upper surface when fully open 64D, lower surface when fully open 63C, color fades to 146C to 146D suffused with 63D on the upper surface and 143C suffused with 63D on the lower surface, upper surface; glabrous, dull, and slightly velvety, lower surface; glabrous and dull, fertile flowers; an average of 12, rotate in arrangement, ovate in shape, acute apex, cuneate base, serrate margin, an average of 2.5 mm in length and 1.5 mm in width, color; upper and lower surfaces when opening and when fully open a mix between 143C and 144B, color does not fade, both surfaces smooth and glabrous.

Reproductive organs:

*Gynoecium*.—Sterile flowers; an average of 4 pistils, an average of 1 mm in length, stigma; club-shaped and 155D in color, style; 0.5 mm in length and 155D in color, ovary is a blend between 155A and 158D in color, fertile flowers; an average of 10 deformed pistils (ranging between 4 to 16 pistils); an average of 1.5 mm in length, stigma; club-shaped and 158D in color, style; 1 mm in length and 65D in color, ovary is 144C in color.

*Androecium*.—Sterile and fertile flowers; not present.

*Fruit and seed*.—No seeds or fruit observed.

It is claimed:

1. A new and distinct cultivar of *Hydrangea* plant named 'Hort 10-087-07' substantially as herein illustrated and described.

* * * * *